(12) United States Patent
Baum et al.

(10) Patent No.: US 7,226,640 B2
(45) Date of Patent: Jun. 5, 2007

(54) METHOD OF FABRICATING IRIDIUM-BASED MATERIALS AND STRUCTURES ON SUBSTRATES

(75) Inventors: Thomas H. Baum, New Fairfield, CT (US); Chongying Xu, New Milford, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 7 days.

(21) Appl. No.: 10/008,980

(22) Filed: Dec. 6, 2001

(65) Prior Publication Data

US 2002/0062037 A1 May 23, 2002

Related U.S. Application Data

(60) Division of application No. 09/453,995, filed on Dec. 3, 1999, now Pat. No. 6,340,769, which is a continuation-in-part of application No. 08/966,797, filed on Nov. 10, 1997, now Pat. No. 6,018,065.

(51) Int. Cl.
*B05D 5/12* (2006.01)
*B05D 3/02* (2006.01)
*C23C 16/00* (2006.01)

(52) U.S. Cl. .......................... 427/229; 427/58; 427/79; 427/255.28

(58) Field of Classification Search ................. 427/58, 427/79, 99, 229, 250, 255.28
See application file for complete search history.

(56) References Cited

U.S. PATENT DOCUMENTS

| | | | | |
|---|---|---|---|---|
| 5,096,737 | A * | 3/1992 | Baum et al. | 427/573 |
| 5,130,172 | A * | 7/1992 | Hicks et al. | 427/252 |
| 5,204,314 | A * | 4/1993 | Kirlin et al. | 505/447 |
| 5,403,620 | A * | 4/1995 | Kaesz et al. | 427/252 |
| 5,536,323 | A * | 7/1996 | Kirlin et al. | 118/726 |
| 5,695,815 | A * | 12/1997 | Vaartstra | 427/226 |
| 5,763,633 | A * | 6/1998 | Vaartstra | 556/136 |
| 5,840,897 | A * | 11/1998 | Kirlin et al. | 546/2 |
| 5,874,364 | A | 2/1999 | Nakabayashi et al. | |
| 6,018,065 | A * | 1/2000 | Baum et al. | 556/136 |
| 6,143,191 | A * | 11/2000 | Baum et al. | 216/63 |
| 6,271,077 | B1 * | 8/2001 | Nakabayashi et al. | 438/240 |
| 6,340,769 | B1 * | 1/2002 | Baum et al. | 556/136 |

OTHER PUBLICATIONS

Leipoldt. et al., "Kinetics of the Substitution Reactions of β-Diketonato-1,5-cyclo octadieneiridium(1) Complexes with Derivatives of 1. 10-Phenanthroline and 2.2'-Dipyridyl." Journal of Organometallic Chemistry, 418, (1991), pp. 241-247.

Basson, et al., "Bromide Catalysts in the Oxidative Addition of Iodomethane to Iridium(I) Complexes," Inoraganica Chimica Acta. 173 (1990) pp. 155-158.

JP08-260148 A (Oct. 8, 1996), col. 2 lines 10-20, col. 6, lines 30-50, Figure (Abstract in English).

Brouwers et al., "Photochemistry of acetylacetanato-, trifluoroacetylacetanato-, and hexafluoroacetyl-acetanato-dicarbonylrhhodium and iridium complexes in frozen gas mixtures at 12K." J. Chem. Soc., Dalton Trans. (1982), (9), 1777-82.

Hitchcock et al., Fluorophosphine Complexes of Rhodium(I) and Iridium(I), J. Chem. Soc. Dalton Trans. (Jul. 1985). pp. 1295-1301, especially p. 129.

Gertin et al. Growth of Iridium Films by Metal Organic Chemical Vapor Deposition. Thin Solid Films. (Apr. 1994), pp. 352-355.

Advanced Inorganic Chemistry by Cotton and Wilkinson, pp. 772.

Cho, H.J. et al., "Preparation and Characterization of Iridium Oxide Thin Films by DC Reactive Sputtering" Extended Abstracts of the 1996 International Conference on Solid State Devices and Materials, Yokohama, (1996). pp. 721-723.

Chen, Tung-Sheng, "Ir-Electroded BST Thin Film Capacitors for 1 Giga-bit DRAM Application", IEEE (1996) pp. 27.2.1-27.2.4.

Nakamura, Takashi et al., "Preparation of $Pb(Zr,Ti)O_3$ Thin Films on Ir and $IrO_2$ Electrodes" Jpn. J. Appl. Phys., Part 1, No. 9B, vol. 33 (1994), pp. 5211-5214.

Chen, Tung-Sheng, "Stability of Reactive DC Sputtered Ir and $IrO_2$ Thin Films in Various Ambients", Integrated Ferroelectrics, vol. 16 (1997), pp. 191-198.

Hoke, J.B., Stern, E.W., Murray, H.H., *J. Mater. Chem.*, 1(4), 551-554 (1991).

Papke, J.A., Stevenson, R.D., *Proc. Conf. Chem. Vapor Dep. of Refractory Metals, Alloys and Compounds*, Gatlinburg, Tennessee, 193-204 (1967).

* cited by examiner

*Primary Examiner*—Brian K. Talbot
(74) *Attorney, Agent, or Firm*—Steven J. Hultquist; Intellectual Property/Technology Law; Maggie Chappuis

(57) ABSTRACT

A method of forming an iridium-containing film on a substrate, from an iridium-containing precursor thereof which is decomposable to deposit iridium on the substrate, by decomposing the precursor and depositing iridium on the substrate in an oxidizing ambient environment which may for example contain an oxidizing gas such as oxygen, ozone, air, and nitrogen oxide. Useful precursors include Lewis base stabilized Ir(I)β-diketonates and Lewis base stabilized Ir(I) β-ketoiminates. The iridium deposited on the substrate may then be etched for patterning an electrode, followed by depositing on the electrode a dielectric or ferroelectric material, for fabrication of thin film capacitor semiconductor devices such as DRAMs, FRAMs, hybrid systems, smart cards and communication systems.

7 Claims, No Drawings

METHOD OF FABRICATING IRIDIUM-BASED MATERIALS AND STRUCTURES ON SUBSTRATES

CROSS-REFERENCE TO RELATED APPLICATION

This is a divisional of U.S. application Ser. No. 09/453,995, filed Dec. 3, 1999, now U.S. Pat. No. 6,340,769; which is a continuation-in-part of U.S. patent application Ser. No. 08/966,797 filed Nov. 10, 1997 in the names of Thomas H. Baum and Chongying Xu for "Method of Fabricating Iridium-Based Materials and Structures on Substrates, and Iridium Source Reagents Therefor," now U.S. Pat. No. 6,018,065.

BACKGROUND OF THE INVENTION

1. Field of the Invention

This invention relates to a method of forming iridium- or iridium-containing materials on substrates, such as Ir-based electrode structures for microelectronic devices and subassemblies, as well as to Ir source reagent materials, and novel dielectric capacitor or ferroelectric material device structures.

2. Description of the Related Art

Iridium (Ir) and iridium oxide ($IrO_2$) are of great interest for use as electrode materials in both dynamic random access memories (DRAMs) and for ferroelectric-based memory devices (FRAMs) which incorporate perovskite metal oxide thin-films as the capacitor layer.

The advantages of Ir over other possible electrode materials include ease of deposition, the ability to "dry etch" the material, the ability to form a stable conducting oxide at high temperatures in an oxidizing environment, and the ability to operate reliably at high temperatures in a working device.

The deposition and processing of Ir-based electrodes is highly desirable in view of the aforementioned advantages. Further, the formation of $IrO_2$ acts as a diffusion barrier to oxidation of conducting polysilicon vias or plugs, as is required in high density DRAM or FRAM devices.

Based on the need for Ir-based electrodes, the art has continued to seek improvements in source materials and deposition techniques for the formation of Ir-based films.

The art has variously disclosed the chemical vapor deposition of iridium for the manufacture of electronic devices in a reducing atmosphere, such as hydrogen gas environment. The art has taught the use of such reducing atmosphere for the purpose of achieving the deposition of element metal iridium for electrodes in applications in which high temperature dielectric materials (e.g., SBT, BST, PZT, PLZT, PNZT, $LaCaMnO_3$, etc., wherein SBT=strontium bismuth tantalate, BST=barium strontium titanate, PZT=lead zironium titanate, PLZT=lead lanthanum zirconium titanate, PNZT=lead niobium zirconium titanate) are deposited on the electrode, to minimize the possibility of degradation of the dielectric in such applications and to concurrently achieve the formation of high purity metal.

The art has especially sought improvements in process technology for the formation of semiconductor and ferroelectric structures that employ Ir electrodes specifically associated with complex dielectric or ferroelectric material layers as thin-film capacitors.

It is an object of the present invention to provide novel source reagents and a process for the formation of iridium-based electrodes that achieve a material simplification in fabrication efficiency and cost, and provide an electrode structure that is highly advantageous for integration with silicon device technology, being efficient, oxygen reactive, oxygen impermeable, and readily fabricated.

It is another object of the invention to provide a simplified method for the fabrication of metal oxide thin film capacitor structures including iridium, iridium oxide or iridium-containing electrode elements, as metal contacts for the oxide DRAM and FRAM devices.

Other objects and advantages of the present invention will be more fully apparent from the ensuing disclosure and appended claims.

SUMMARY OF THE INVENTION

This invention relates to a method of forming iridium- or iridium-containing materials on substrates, such as Ir-based electrode structures for microelectronic devices and subassemblies, and catalytic materials, as well as to Ir source reagent materials, and novel dielectric material structures.

As used herein, the term "Ir-based" or "iridium-based" refers broadly to elemental iridium, iridium oxide, iridium-containing material compositions and combinations thereof.

The present invention also relates to novel high temperature dielectric or ferroelectric thin film capacitor structures including Ir-based electrode elements.

In one aspect, the invention relates to a method of forming an iridium-containing film on a substrate, from an iridium-containing precursor thereof that is decomposed to deposit iridium on the substrate, such method comprising decomposing the precursor and depositing iridium on the substrate in an oxidizing ambient environment. The deposition of iridium on the substrate may be carried out in any suitable manner and by any appropriate techniques of the art, including chemical vapor deposition (CVD), assisted CVD, or physical deposition methods such as ion plating, rapid thermal processing, molecular beam epitaxy, etc.

As used herein, the term "oxidizing ambient environment" means an environment including oxygen-containing gas, such as oxygen, ozone, air, nitrogen oxide ($NO_x$), or the like. Such oxidizing atmosphere may be provided in a deposition chamber or reaction vessel in which the deposition is carried out, and enables the formation of iridium or iridium oxide on the substrate. Accordingly, the deposition may be conducted in an ambient air environment, thereby simplifying the formation of the iridium-containing film on the substrate. In an alternate embodiment, $IrO_2$ may be formed in a post-deposition process from Ir metal by treatment in an oxidizing environment.

The Ir precursor material may be of any suitable composition and type. In preferred practice of the present invention, the precursor may suitably comprise a Lewis base-stabilized β-diketonate iridium composition or a Lewis base-stabilized beta-ketoiminate composition, as hereafter more fully described.

When the iridium-containing film is employed to form an electrode or other patterned structure on the substrate, the deposited iridium or iridium oxide film may be dry etched with a halogen-based plasma and/or preferably, $XeF_2$, as more fully described in concurrently filed U.S. patent application Ser. No. 08/966,796 filed Nov. 10, 1997 in the names of Thomas H. Baum and Frank DiMeo, Jr., for "Method for Etch Fabrication of Iridium-Based Electrode Structures," the disclosure of which hereby is incorporated herein in its entirety. In such dry etching of a deposited iridium or iridium oxide film, the etch rates can optionally be enhanced through the use of Lewis-based adducts or electron backbonding species such as carbon monoxide, trifluorophosphine, trialkylphosphines or other suitable Lewis base.

In yet another aspect of the present invention, the iridium-containing film subsequent to its formation as an electrode structure may have deposited thereon a high temperature dielectric and/or ferroelectric material. An oxidizing ambient environment may be employed for the deposition of the iridium-containing film or may be used solely during the deposition of the oxide dielectric/ferroelectric.

It may therefore be unnecessary to purge the chamber of a reducing atmosphere, or to transfer the substrate article bearing the iridium-containing film from the iridium deposition chamber to a dielectric/ferroelectric deposition chamber, as has been done in the prior art to accommodate the usage of hydrogen or other reducing gas (forming gas) atmospheres in the iridium electrode formation step.

The method of this invention therefore achieves a substantial simplification of the procedure for forming a capacitor or other microelectronic device in which the iridium-containing electrode is overcoated with a dielectric or ferroelectric material.

Another aspect of the invention relates to a microelectronic device structure comprising an iridium oxide electrode element overcoated by a high temperature dielectric, e.g., SBT, PZT, BST, PLZT, PNZT, $LaCaMnO_3$, etc., wherein the electrode is conductively operative in relation to the high temperature dielectric. As used herein, high temperature dielectric refers to a dielectric material deposited on the electrode at a temperature above about 300° C. By way of example, dielectric films of lead zirconium titanate (PZT) are typically deposited at temperatures on the order of 500–600° C.

Yet another aspect of the invention relates to a composition comprising an organic solvent solution of an Ir(I) reagent, wherein the Ir(I) reagent is selected from the group consisting of:

Lewis base stabilized Ir(I) β-diketonates of formula I:

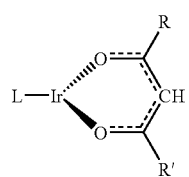

wherein R and R' may be alike or different and may be H, aryl, perfluoroaryl, $C_1$–$C_6$ alkyl, or $C_1$–$C_6$ perfluoroalkyl, and L is a coordinating Lewis base; and Lewis base stabilized Ir(I) β-ketoiminates of formula II:

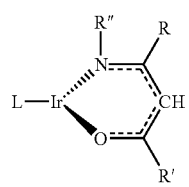

wherein R, R', and R" are the same or different, and are independently selected from the group consisting of H, aryl, perfluoroaryl, $C_1$–$C_6$ alkyl, or $C_1$–$C_6$ perfluoroalkyl, and L is a coordinating Lewis base; and the organic solvent solution comprises a non-polar solvent, such as $C_5$–$C_{12}$ hydrocarbon alkanes (e.g., hexane, heptane, octane, nonane and decane) and $C_6$–$C_{10}$ hydrocarbon aryls (e.g., benzene, toluene and xylene).

Yet another aspect of the invention relates to a composition comprising a non-polar solvent solution of a cyclooctadiene (COD) adduct of an Ir(I) beta-diketonate.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The following patents and patent applications are hereby incorporated herein by reference in their respective entireties:

U.S. patent application Ser. No. 08/966,796 filed Nov. 10, 1997 in the names of Thomas H. Baum and Frank DiMeo, Jr., for "Method for Etch Fabrication of Iridium-Based Electrode Structures;"

U.S. Pat. No. 5,840,897 issued Nov. 24, 1998 in the names of Peter S. Kirlin, Duncan W. Brown, Thomas H. Baum, Brian A. Vaartstra and Robin A. Gardiner for "Metal Complex Source Reagents for Chemical Vapor Deposition;"

U.S. patent application Ser. No. 08/484,654 filed Jun. 7, 1995 in the names of Robin A. Gardiner, et al. for "Method of Forming Metal Films on a Substrate by Chemical Vapor Deposition;"

U.S. Pat. No. 5,820,664 issued Oct. 13, 1998 in the names of Robin A. Gardiner et al. for "Precursor Compositions for Chemical Vapor Deposition, and Ligand Exchange Resistant Metal-Organic Precursor Solutions Comprising Same;"

U.S. Pat. No. 5,204,314 issued Apr. 20, 1993 in the names of Peter S. Kirlin, et al. for "Method for Delivering an Involatile Reagent in Vapor Form to a CVD Reactor;"

U.S. Pat. No. 5,453,494 issued Sep. 26, 1995 in the names of Peter S. Kirlin, et al. for "Metal Complex Source Reagents for MOCVD;"

U.S. Pat. No. 5,916,359 issued Jun. 29, 1999 in the names of Thomas H. Baum, et al. for "Alkane and Polyamine Solvent Compositions for Liquid Delivery Chemical Vapor Deposition;"

U.S. Pat. No. 5,923,970 issued Jul. 13, 1999 in the names of Peter S. Kirlin, et al. for Method of Fabricating a Ferroelectric Capacitor with a Graded Barrier Layer Structure;" and U.S. Pat. No. 5,719,417 issued Feb. 17, 1998 in the names of Jeffrey Roeder, et al. for "Ferroelectric Integrated Circuit Structure."

As used herein, the term "Lewis base" means a compound or chemical moiety that forms a bond by donating a pair of electrons. The compositions of the present invention containing the Lewis base constituent are understood to be devoid of other components that preclude the electron donor character of the Lewis base constituent from being present.

With respect to the Ir(I) precursor compositions of the invention, as hereinafter more fully described, it is to be appreciated that the compositions may be specifically characterized as comprising, consisting or consisting essentially of the constituents specifically referenced or described herein, and such compositions may specifically be characterized as being free, substantially free or devoid of any constituents not specifically referenced or described herein, as may be claimed hereinafter at any time during the proceedings involving the application hereof, or an application based hereon.

The present invention relates to the discovery that Ir-based electrode structures can be readily formed without the necessity of depositing the Ir component from a precursor or source material in a reducing atmosphere, as has heretofore been the approach and objective of the prior art.

Contrariwise, the present invention contemplates a method of forming an iridium-containing film on a substrate, from an iridium-containing precursor thereof which is decomposed to deposit iridium on the substrate, in which the decomposition of the precursor and the deposition of iridium on the substrate is carried out in an oxidizing ambient environment to deposit iridium in the form of iridium per se or in the form of iridium oxide.

Iridium may be deposited on the substrate in the method of the present invention in any suitable manner, including chemical vapor deposition, liquid delivery, sputtering, ablation, or any other suitable technique known in the art for deposition of metal on a substrate from a metal-organic or other precursor source material. Among the foregoing, chemical vapor deposition is preferred when the iridium-based structures being formed have critical dimensions below about 0.5 microns.

In the method of the invention, the precursor for the iridium component may be any suitable iridium precursor compound, complex or composition that is advantageous for yielding iridium for deposition on the substrate. The iridium precursor may for example comprise a Lewis base-stabilized β-diketonate iridium composition or a Lewis base-stabilized β-ketoiminate composition, of the formulae:

Lewis base stabilized Ir(I) β-diketonates of formula I:

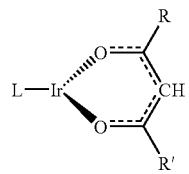

I wherein R and R' are the same or different and may be H, aryl, perfluoroaryl, $C_1$–$C_6$ alkyl, or $C_1$–$C_6$ perfluoroalkyl, and L is a coordinating Lewis base, preferably alkene, diene, cycloalkene, cyclodiene, cyclooctatetraene, alkyne, substituted alkyne (symmetrical or asymmetrical), amine, diamine, triamine, tetraamine, ether, tetrahydrofuran, glyme, diglyme, triglyme, tetraglyme, phosphine, carbonyl, dialkyl sulfide, vinyltrimethylsilane, and allyltrimethylsilane, or Lewis base stabilized Ir(I) β-ketoiminates of formula II:

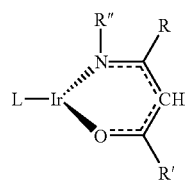

II wherein R, R', and R" are the same or different, and are independently selected from the group consisting of H, aryl, perfluoroaryl, $C_1$–$C_6$ alkyl, or $C_1$–$C_6$ perfluoroalkyl, and L is a coordinating Lewis base, preferably selected from the group consisting of alkene, diene, cycloalkene, cyclodiene, cyclooctatetraene, alkyne, substituted alkyne (symmetrical or asymmetrical), amine, diamine, triamine, tetraamine, ether, tetrahydrofuran, glyme, diglyme, triglyme, tetraglyme, phosphine, carbonyl, dialkyl sulfide, vinyltrimethylsilane, and allyltrimethylsilane.

For the Lewis base in the above precursors of formulae I and II, one or more Lewis base molecules may be preferred, especially for ether, cyclic ether, tetrahydrofuran, alkene, alkyne, carbonyl and phosphine ligands. In some embodiments of precursors of formula II, R and R' may be identical and R" will be independently selected from the substituents listed above.

In CVD-based embodiments of the present invention, either a bubbler or organic solution liquid delivery can be utilized for the chemical vapor deposition of the Ir/$IrO_2$ thin film. The specific precursor may be suitably optimized for the delivery and transport of the precursor to the CVD reactor. The precursor is decomposed in the presence of an oxidant (e.g., $O_2$, $O_3$, or $N_2O$) to preferentially deposit the metal Ir (<500° C.) or the oxide, $IrO_2$ (>550° C.). In some applications, the formation of a bi-layered Ir/$IrO_2$ film may be preferred.

The etching of Ir and $IrO_2$ in the practice of the invention, after the initial formation of the iridium-containing film, may be carried out with the use of halogen-based systems, such as chlorine, bromine, and fluorine based plasma or ion beam etch chemistries. The formation of halogens of Ir(I) and Ir(III) can be exploited to etch and pattern electrodes for semiconductor and ferroelectric device applications. In systems where $IrO_2$ is present, the use of either a reducing pre-treatment (to return the iridium oxide to Ir metal) or the use of fluorine etchants may be preferred. The formation and removal of etch by-products depends on the volatility of the halide species. The addition of stabilizing co-reactants may usefully be employed to facilitate the removal and etching of the materials.

The iridium-containing films deposited in accordance with the method of the present invention may be etched with a dry etch method, as more fully described in the aforementioned co-pending U.S. patent application Ser. No. 08/966, 796 filed Nov. 10, 1997 in the names of Thomas H. Baum and Frank DiMeo Jr. for "Method for Etch Fabrication of Iridium-Based Electrode Structures," optionally using specific chemical enhancements to the rate of etching. The addition of carbon monoxide, trifluorophosphine, or trialkyl phosphines can accelerate the rate of etching by enhancing the volatility of the produced etch by-products.

For example, in the etching of the Ir-containing film on the substrate, the removal rate for the process may be advantageously accelerated by the presence of carbon monoxide (CO). The rates are strongly dependent upon the gas-phase partial pressure of the reactants in elevated substrate temperature regimes (e.g., 725–975° C.). The presence of CO may serve to enhance the reactant volatility through the formation of $(CO)_yIrX_3$ (where X=Cl, Br) and for $Ir(Cl)_4$. $IrF_6$ may also be employed for such purpose. These materials can be used advantageously for etching Ir in halogen-based plasmas, ion beams and in hybrid etching schemes.

In some instances, it may be desirable to convert the iridium oxide material deposited on the substrate to a pure iridium metal for a specific fabrication or device application. In such instance, the deposited film of iridium oxide may be exposed to a reducing gas, such as hydrogen, forming gas, CO, ROH, etc, to effect such conversion.

After its formation and any additional patterning, the iridium-containing electrode may have deposited thereon a high temperature dielectric and/or ferroelectric material in the same oxidizing ambient environment employed for the deposition of the iridium-containing film.

It is therefore unnecessary to purge the chamber of a reducing atmosphere, or to transfer the substrate article bearing the iridium-containing film from the iridium deposition chamber to a dielectric/ferroelectric deposition chamber, as has been done in the prior art to accommodate the usage of hydrogen or other reducing gas (forming gas) atmospheres in the iridium electrode formation step. The method of the invention therefore achieves a substantial simplification of the procedure for forming a capacitor or other microelectronic device in which the iridium-containing electrode is overcoated with a dielectric or ferroelectric material.

The iridium films deposited in the practice of the present invention may therefore be utilized for the formation of electrode and other elements of semiconductor devices, such as for example DRAMs, FRAMs, hybrid systems, smart cards and communication systems, as well as any other applications in which the thin films of iridium and/or iridium oxide are advantageously employed, such as catalytic systems.

As a specific example of an Ir(I) precursor composition that may be usefully employed in the broad practice of the present invention, a precursor comprising a cycloalkenyl moiety such as the cyclooctadiene (COD) adduct of Ir(I) beta-diketonate, in a suitable hydrocarbon solvent (octane), may be employed for liquid delivery MOCVD of iridium for electrode formation in the manufacture of semiconductor devices such as those mentioned in the preceding paragraph.

The hydrocarbon solvents useful for such purpose may for example include non-polar solvents, e.g., $C_5$–$C_{12}$ alkane solvents such as hexane, octane, etc., $C_1$–$C_8$ alkyl-substituted benzene solvents, e.g., toluene, xylene or other hydrocarbon substituted solvents, e.g., diethylether or tetrahydrofuran, etc. The solvent medium for the cyclooctadiene (COD) adduct of Ir(I) beta-diketonate desirably does not include alkanolic solvents (e.g., ethanol and isopropanol) since the presence of such solvents may lead to premature decomposition of the source reagent complex in solution, prior to delivery or during vaporization of the precursor mixture.

As used herein, the term "non-polar solvent" means a hydrocarbon alkane(s) or aryl solvent having a dielectric constant ($\in$) of from about 1 to about 15. The dielectric constant provides a measure of the solvent's capacity to separate ionic charge, so that the higher the value of the dielectric constant, the more polar the solvent. Further, these solvents are characterized by being primarily hydrocarbons without the presence of polar substituents, such as oxygen, sulfur, chlorine, bromine, fluorine and other polarizable groups.

The β-diketonate ligand in such cyclooctadiene (COD) adduct of Ir(I) β-diketonate may be of any suitable type, including the illustrative β-diketonate ligand species set out in Table A below:

TABLE A

| Beta-diketonate ligand | Abbreviation |
|---|---|
| 2,2,6,6-tetramethyl-3,5-heptanedionato | thd |
| 1,1,1-trifluoro-2,4-pentanedionato | tfac |
| 1,1,1,5,5,5-hexafluoro-2,4-pentanedionato | hfac |
| 6,6,7,7,8,8,8-heptafluoro-2,2-dimethyl-3,5-octanedionato | fod |
| 2,2,7-trimethyl-3,5-octanedionato | tod |

TABLE A-continued

| Beta-diketonate ligand | Abbreviation |
|---|---|
| 1,1,1,5,5,6,6,7,7,7-decafluoro-2,4-heptanedionato | dfhd |
| 1,1,1-trifluoro-6-methyl-2,4-heptanedionato | tfmhd |

The liquid delivery MOCVD system for growing the iridium films of the invention may for example comprise a system of the type disclosed in U.S. Pat. No. 5,204,314 issued Apr. 20, 1993 to Peter S. Kirlin et al. and in U.S. Pat. No. 5,536,323 issued Jul. 16, 1996 to Peter S. Kirlin et al., which utilize heated vaporization structures such as microporous disk elements to effect high rate vaporization of the source reagent materials for the metal oxide film. In operation, liquid source reagent compositions are flowed onto the vaporization structure for flash vaporization. Vapor thereby is produced for transport to the deposition zone, e.g., the CVD reactor. The liquid delivery systems of these patents provide high efficiency generation of vapor from which films may be grown on substrates.

The precursor vapor formed by the high rate vaporization apparatus is transported to a chemical vapor deposition zone containing a substrate, e.g., a wafer provided on a heated susceptor. Upon contacting of the precursor vapor with the wafer, the metal components of the vapor are deposited on the wafer surface. The vapor may be delivered in the chemical vapor deposition chamber by a disperser such as a showerhead or nozzle, to provide a uniform flux of the vapor across the width of the wafer, to yield a correspondingly uniform thickness of deposited metal-containing film on the wafer. The process conditions (temperature, pressure, flow rate and composition of the vapor) may be suitably controlled to ensure an optimum process result for the specific MOCVD operation being conducted in the process system.

While the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A method of forming an iridium-containing film on a substrate, comprising use of an organic solvent solution, said organic solvent solution comprising an iridium-containing precursor that is decomposable to deposit iridium on the substrate, said method comprising decomposing the precursor from said solution and depositing iridium on the substrate in an oxidizing ambient environment, wherein the precursor comprises a composition selected from the group consisting of:

Lewis base stabilized Ir(I) β-diketonates of formula I:

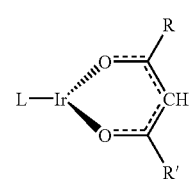

wherein R and R' may be alike or different and may be H, aryl, perfluoroaryl, $C_1$–$C_6$ alkyl, or $C_1$–$C_6$ perfluoroalkyl, and L is a coordinating Lewis base; and Lewis base stabilized Ir(I) β-ketoiminates of formula II:

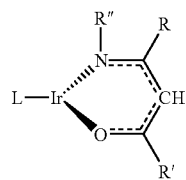

wherein R, R', and R" are the same or different, and are independently selected from the group consisting of H, aryl, perfluoroaryl, $C_1$–$C_6$ alkyl, or $C_1$–$C_6$ perfluoroalkyl, and L is a coordinating Lewis base.

2. A method of forming an iridium-containing film on a substrate, from an iridium-containing precursor thereof that is decomposable to deposit iridium on the substrate, said method comprising decomposing the precursor and depositing iridium on the substrate in an oxidizing ambient environment, wherein the precursor comprises a composition selected from the group consisting of:

Lewis base stabilized Ir(I) β-diketonates of formula I:

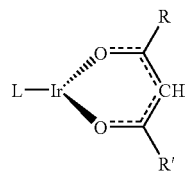

wherein R and R' may be alike or different and may be H, aryl, perfluoroaryl, $C_2$–$C_6$ alkyl, or $C_1$–$C_6$ perfluoroalkyl, and L is a coordinating Lewis base.

3. A method of forming an iridium-containing film on a substrate, from an iridium-containing precursor thereof that is decomposable to deposit iridium on the substrate, said method comprising decomposing the precursor and depositing iridium on the substrate in an oxidizing ambient environment, wherein the precursor comprises a composition selected from the group consisting of:

Lewis base stabilized Ir(I) β-ketoiminates of formula II:

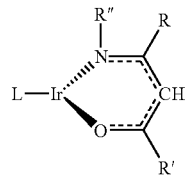

wherein R, R', and R" are the same or different, and are independently selected from the group consisting of H, aryl, perfluoroaryl, $C_1$–$C_6$ alkyl, or $C_1$–$C_6$ perfluoroalkyl, and L is a coordinating Lewis base.

4. A method of forming a microelectronic device or precursor structure on a substrate, including an electrode operatively associated with a high-temperature dielectric or ferroelectric material deposited thereover, said method comprising:

(A) forming an iridium-containing film on the substrate, comprising use of an organic solvent solution, said organic solvent solution comprising an iridium-containing precursor which is decomposable to deposit iridium on the substrate, comprising:

(i) decomposing the precursor from said solution and depositing iridium on the substrate in an oxidizing ambient environment; and (ii) processing the deposited iridium into an iridium-based electrode element; and (B) depositing on the iridium-based electrode element a high temperature dielectric and/or ferroelectric material, wherein the iridium-containing precursor comprises a composition selected from the group consisting of:

Lewis base stabilized Ir(I) β-diketonates of formula I:

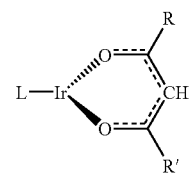

wherein R and R' may be alike or different and may be H, aryl, perfluoroaryl, $C_1$–$C_6$ alkyl, or $C_1$–$C_6$ perfluoroalkyl, and L is a coordinating Lewis base; and Lewis base stabilized Ir(I) β-ketoiminates of formula II:

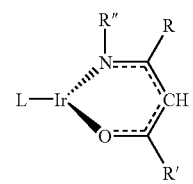

wherein R, R', and R" are the same or different and are independently selected from the group consisting of H, aryl, perfluoroaryl, $C_1$–$C_6$ alkyl, or $C_1$–$C_6$ perfluoroalkyl, and L is a coordinating Lewis base.

5. The method of claim 1, wherein said organic solvent solution comprises a non-polar solvent selected from the group consisting of $C_5$–$C_{12}$ hydrocarbon alkanes and $C_6$–$C_{10}$ hydrocarbon aryls.

6. The method of claim 4, wherein said organic solvent solution comprises a non-polar solvent selected from the group consisting of $C_5$–$C_{12}$ hydrocarbon alkanes and $C_6$–$C_{10}$ hydrocarbon aryls.

7. The method according to claim 4, wherein the oxidizing ambient environment comprises air.

* * * * *

UNITED STATES PATENT AND TRADEMARK OFFICE
CERTIFICATE OF CORRECTION

PATENT NO.        : 7,226,640 B2
APPLICATION NO.   : 10/008980
DATED             : June 5, 2007
INVENTOR(S)       : Baum et al.

It is certified that error appears in the above-identified patent and that said Letters Patent is hereby corrected as shown below:

Title page, item 56, OTHER PUBLICATIONS, second column, line 14: "especially p. 129" should be -- especially p. 1297 --.

Title page, item 56, OTHER PUBLICATIONS, second column, line 15: "Gertin" should be -- Gerfin --.

Column 5, line 15; "per se" should be -- *per se* --

Column 6, line 17: "$o_3$" should be -- $O_3$ --

Column 9, line 16 (claim 1): "Lewis base" should be -- Lewis base selected from the group consisting of alkene, diene, cycloalkene, cyclodiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane and allytrimethlysilane --.

Column 9, line 38 (claim 2): "Lewis base" should be -- Lewis base selected from the group consisting of alkene, diene, cycloalkene, cyclodiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane and allytrimethlysilane --.

Column 9, line 61 (claim 3): "Lewis base" should be -- Lewis base selected from the group consisting of alkene, diene, cycloalkene, cyclodiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane and allytrimethlysilane --.

Column 10, line 34 (claim 4): "Lewis base" should be -- Lewis base selected from the group consisting of alkene, diene, cycloalkene, cyclodiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane and allytrimethlysilane --.

UNITED STATES PATENT AND TRADEMARK OFFICE
CERTIFICATE OF CORRECTION

PATENT NO. : 7,226,640 B2
APPLICATION NO. : 10/008980
DATED : June 5, 2007
INVENTOR(S) : Baum et al.

It is certified that error appears in the above-identified patent and that said Letters Patent is hereby corrected as shown below:

Column 10, line 50 (claim 4): "Lewis base" should be -- Lewis base selected from the group consisting of alkene, diene, cycloalkene, cyclodiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane and allytrimethlysilane --.

Signed and Sealed this

Thirty-first Day of July, 2007

JON W. DUDAS
*Director of the United States Patent and Trademark Office*